United States Patent [19]

Inamoto et al.

[11] 4,078,085
[45] Mar. 7, 1978

[54] 3-AMINOMETHYL-4-HOMOISOTWISTANE AND ITS SALT AND PROCESS FOR PRODUCING SAME

[75] Inventors: Yoshiaka Inamoto; Yoshiaka Fujikura; Hiroshi Ikeda, all of Wakayama; Naotake Takaishi, Iwade, all of Japan

[73] Assignee: Kao Soap Co., Ltd., Tokyo, Japan

[21] Appl. No.: 700,155

[22] Filed: Jun. 28, 1976

[30] Foreign Application Priority Data

Aug. 6, 1975  Japan .................. 50-95562

[51] Int. Cl.² ............... A61K 31/13; C07C 87/32
[52] U.S. Cl. .................... 424/325; 260/563 P
[58] Field of Search ............ 260/563 P; 424/325

[56] References Cited

U.S. PATENT DOCUMENTS

| | | | |
|---|---|---|---|
| 3,397,233 | 8/1968 | Cairns | 260/563 P |
| 3,449,422 | 6/1969 | Miller | 260/563 P |
| 3,470,248 | 9/1969 | Brotherton et al. | 260/563 P |
| 3,729,513 | 4/1973 | Berezin | 260/563 P X |

OTHER PUBLICATIONS

Aigami et al., "J. Med. Chem.", 19, 536 (1976).

Primary Examiner—Paul F. Shaver
Attorney, Agent, or Firm—Oblon, Fisher, Spivak, McClelland & Maier

[57] ABSTRACT

3-Aminomethyl-4-homoisotwistane acid addition salts produced by the steps of reducing 4-homoisotwistane-3-carboxylic acid amide or 4-homoisotwistyl-3-cyanide represented by the following general formula, and converting 3-aminomethyl-4-homoisotwistane into its addition salt-wherein R stands for the group of the formula —CONH$_2$ or —CN.

3 Claims, No Drawings

3-AMINOMETHYL-4-HOMOISOTWISTANE AND ITS SALT AND PROCESS FOR PRODUCING SAME

This invention relates to novel 3-aminomethyl-4-homoisotwistane (3-aminomethyl-tricyclo [5.3.1.0$^{3,8}$] undecane) represented by the following formula [I]:

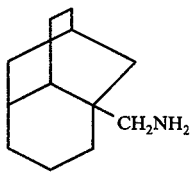

and an acid addition salt thereof, and to a process for producing the same.

The compound of the formula [I] and an acid addition salt thereof have been first synthesized by the present inventors. These are the derivatives of 4-homoisotwistane (tricyclo [5.3.1.0$^{3,8}$] undecane) into which is introduced an aminomethyl group. The compounds have not been found in any literature.

The present inventors have examined a wide variety of 4-homoisotwistane derivatives having a cage structure similar to that of naturally occurring sesqui terpene and, as a result, found that 3-aminomethyl-4-homoisotwistane of the formula [I] and an acid addition salt thereof exhibit an excellent antiviral activity.

SUMMARY OF THE INVENTION

One object of this invention is, therefore, to provide novel 3-aminomethyl-4-homoisotwistane represented by the formula [I] and an acid addition salt thereof.

Another object of this invention is to provide 3-aminomethyl-4homoisotwistane and an acid addition salt thereof which are useful as an antiviral agent.

A further object of this invention is to provide a process for advantageously producing these compounds.

DETAILED DESCRIPTION OF THE PREFERRED EMBODIMENTS

According to the present invention, 3-aminomethyl-4-homoisotwistane of the formula [I] is produced by reducing 4-homoisotwistane-3-carboxylic acid amide (R stands for an aminocarbonyl group in the formula [II]) or 4-homoisotwistyl-3-cyanide (R stands for a cyano group in the formula [II]), as is shown by the following reaction formula:

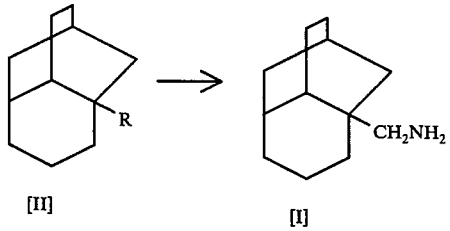

wherein R stands for the group of the formula, —CONH$_2$ or —CN.

The starting material of the formula [II] according to the invention may be produced, as for example, by reacting 4-homoisotwistane with t-butyl alcohol and formic acid, or with carbon monoxide in the presence of sulfuric acid, to form 4-homoisotwistane-3-carboxylic acid, and halogenating the resulting compound to form 4-homoisotwistane-3-carboxylic acid halide and subsequently reacting the halide with ammonia to obtain 4-homoisotwistane carboxylic acid amide. Another advantageous method is to subject the thus obtained amide to the dehydration reaction to obtain 4-homoisotwistyl-3-cyanide.

In carrying out the inventive process, the compound of the formula [II] is either reacted with a metal hydride such as lithium aluminum hydride or subjected to the catalytic reduction in the presence of a reducing agent.

In case the metal hydride is employed, it may preferably be used in equivalency to an excessive amount of about 20%. An excess of the amount described above is also useful without any trouble.

A solvent to be used for the process of this invention can be selected from ethers such as diethylether, tetrahydrofuran and the like which are commonly used in the reduction by a metal hydride. The reaction is carried out at a temperature of −20° to +150° C, particularly under reflux condition to afford better results.

A reducing agent to be used in catalytic reduction can be selected, for example, from Raney nickel, copper-chromium oxide, platinum oxide and the like.

In case 4-homoisotwistyl-3-cyanide is employed as a starting material, the reaction may be conducted with Raney nickel or platinum oxide in an amount of 0.1 − 20% by weight of the raw material at a hydrogen pressure ranging from 30 to 200 atm. A solvent for this reaction can be selected, for example, from ethanol, acetic acid, acetic anhydride, dioxane and the like, and the reaction is preferably conducted at a temperature of room temperature to 150° C. In the case where Raney nickel catalyst is used, the reaction may be conducted in the presence of ammonia and/or alkali hydroxide to improve yields.

In case 4-homoisotwistane-3-carboxylic acid amide is employed as a starting material, the reaction may be preferably conducted with the use of copper-chromium oxide catalyst in ethers such as dioxane, tetrahydrofuran and the like in the range of 50° to 300° C, particularly at a temperature of 100° to 250° C, and under a hydrogen pressure ranging from 100 to 300 atm.

An acid addition salt of the thus obtained 3-aminomethyl-4-homoisotwistane is produced by known methods, that is, by neutralization with acids.

The antiviral effect of 3-aminomethyl-4-homoisotwistane is described with the experimental results.

After chick embryo fibroblast cells were cultured in a test tube for 2 to 3 days, the medium was inoculated with Newcastle disease virus of about 128HAU (Hemagglutination Unit). To the upper layer was added a culture medium of the stepwise dilution system containing the following compounds, then the resulting mixture was cultured at 37° C for 48 hours and the effects were evaluated based on the hemagglutination reaction.

The results obtained are shown in Table 1.

Table 1

| Compounds | Concentration (mg/ml) | % HAU* | CT** |
| --- | --- | --- | --- |
| | 40 | < 0.2 | + |
| | 20 | 1.1 | ± |
| 3-Aminomethyl-4- | 10 | 7.5 | — |
| homoisotwistane hydrochloride | 5 | 43 | — |
| | 2.5 | 43 | — |
| | 500 | < 1.0 | + |

Table 1-continued

| Compounds | Concentration (mg/ml) | % HAU* | CT** |
|---|---|---|---|
| Adamantylamine | 250 | 9 | + |
| hydrochloride | 125 | 100 | — |
| (control) | 62 | 100 | — |

*% HAU = $\dfrac{\text{HAU in the media containing the compounds (Dilution multiple inhibiting hemagglutination)}}{\text{HAU in the blank medium}} \times 100$

**CT Degree of damage on chick embryo fibroblast cells caused by the test compounds
— No damage observed
± Small eruptions observed on the surface of the cell
+ Monolayers of chick embryo fibroblast cells separated from the wall of tube The inventive process according to the invention is hereinafter described more specifically in terms of several Examples which, however, are intended to explain and not to impose limitations upon the invention.

EXAMPLE 1

To tetrahydrofuran dried over metal sodium was added 0.5 g (13.2m moles) of lithium alumium hydride. To the resulting mixture was added dropwise with stirring a solution of tetrahydrofuran and 1.45g (7.5m moles) of 4-homoisotwistane-3-carboxylic acid amine over a period of 15 minutes, and the mixture was then stirred under reflux for 4 hours. After the completion of the reaction, the mixture was cooled and subsequently subjected to addition of ethyl acetate and water to decompose the excess lithium aluminum hydride. The mixture was extracted three times with 30ml of diethyl ether, and the ether layer was extracted three times with 20ml of 10% hydrochloric acid. To the aqueous layer was added a sodium hydroxide solution in such an amount that the solution became alkaline to some extent, and the resulting mixture was extracted three times with 30ml of diethyl ether. The ethereal extract was dried over anhydrous sodium sulfate. Since 3-aminomethyl-4-homoisotwistane [I] formed is so hygroscopic, the ethereal solution was filtered and then dry hydrogen chloride was bubbled into the filtrate. The solvent was evaporated to obtain 1.1g (Yield 68%) of the hydrochloride of the compound [I] as a white precipitate having a melting point of 255° – 260° C (decomposition, in a sealed tube).

Elemental Analysis: as $C_{12}H_{22}NCl$ Calculated (%): C: 66.8; H: 10.3; N; 6.5; Cl: 16.4 Found (%): C: 66.4; H: 10.0; N: 6.3; Cl: 15.9 ir (nujol, $cm^{-1}$): 1600, 1500 ms, m/e (relative strength): 179(16), 149(77), 93(16), 81(33), 79(19), 67(51), 41(19), 30(49), 18(100), 17(32)

In a mass spectrum, a parent peak as 3-aminomethyl-4-homoisotwistane hydrochloride was not recognized, but a peak corresponding to 3-aminomethyl-4-homoisotwistane free of acid was observed as the maximum mass peak. This was in accord with the result of the mass spectrum with 3-aminomethyl-4-homoisotwistane collected by gaschromatography from the ether extract before bubbling of hydrogen chloride.

EXAMPLE 2

A mixture of 1.75g (10m moles) of 4-homoisotwistyl-3-cyanide, 90mg of Raney nickel, 50mg of 40% sodium hydroxide solution and 20ml of 98% ethanol as a solvent was placed in an autoclave and hydrogenated at 115° – 120° C for 2 hours while a pressure of hydrogen was kept at 120 kg/cm². After cooling, the mixture was filtered to separate the catalyst, and the filtrate was evaporated to obtain the residue, which was extracted twice with 20ml of diethylether.

The ethereal layer was washed once with 20ml of water and then dried over anhydrous sodium sulfate. This was filtered and dry hydrogen chloride was bubbled into the filtrate. Removal of the solvent from the mixture presented 1.4g (Yield 65%) of 3-aminomethyl-4-homoisotwistane hydrochloride as a white solid.

What we claim is:

1. 3-Aminomethyltricyclo [5.3.1.0$^{3,8}$] undecane and acid addition salts thereof.

2. The compound of claim 1, wherein said acid addition salt is a hydrochloride.

3. A pharmaceutical composition which comprises an antiviral amount of a compound of claim 1 and a pharmaceutically acceptable adjuvant.

* * * * *